(12) United States Patent
Mugan et al.

(10) Patent No.: US 11,488,723 B1
(45) Date of Patent: Nov. 1, 2022

(54) FEATURE PREDICTION

(71) Applicant: Pulselight Holdings, Inc., Austin, TX (US)

(72) Inventors: Jonathan Mugan, Buda, TX (US); Mallika Thanky, Chicago, IL (US)

(73) Assignee: Pulselight Holdings, Inc., Austin, TX (US)

( * ) Notice: Subject to any disclaimer, the term of this patent is extended or adjusted under 35 U.S.C. 154(b) by 0 days.

(21) Appl. No.: 16/430,035

(22) Filed: Jun. 3, 2019

Related U.S. Application Data

(60) Provisional application No. 62/680,431, filed on Jun. 4, 2018.

(51) Int. Cl.
*G16H 50/70* (2018.01)
*G16H 10/60* (2018.01)
*G16H 50/20* (2018.01)
*G16B 40/00* (2019.01)
*G06F 17/18* (2006.01)

(52) U.S. Cl.
CPC ............. *G16H 50/70* (2018.01); *G06F 17/18* (2013.01); *G16B 40/00* (2019.02); *G16H 10/60* (2018.01); *G16H 50/20* (2018.01)

(58) Field of Classification Search
CPC ........ G06N 20/00; G16H 50/20; G16H 50/30; G16H 10/60; G16H 50/70
See application file for complete search history.

(56) References Cited

U.S. PATENT DOCUMENTS

2017/0330109 A1* 11/2017 Maughan ................. G06N 5/04
2018/0052961 A1* 2/2018 Shrivastava ........... G06N 20/00

FOREIGN PATENT DOCUMENTS

WO WO-2016016459 A1 * 2/2016 ........... G06F 19/321

OTHER PUBLICATIONS

Li, X., et al. "Using machine learning to predict opioid overdoses among prescription opioid users." Value in Health 21 (2018): S245. Published May 2018 (Year: 2018).*
Aggarwal, CC et al. On the Surprising Behavior of Distance Metrics in High Dimensional Space. In: Van den Bussche J., et al. (eds) Database Theory—ICDT 2001, Lecture Notes Computer Science vol. 1973 (Springer-Verlag Berlin Heidelberg 2001).
(Continued)

*Primary Examiner* — Linh Giang Le
*Assistant Examiner* — Constantine Siozopoulos
(74) *Attorney, Agent, or Firm* — J. Roger Williams, Jr.

(57) ABSTRACT

A method for generating synthetic training records for use in training a model to predict low-incidence events. A synthetic training record is generated from a minority-class training record by substituting a different value for a feature in the minority-class training record, where the probability of the different value occurring in the minority-class training record exceeds a probability threshold. Also disclosed are a non-transitory storage medium comprising minority-class training records and synthetic training records and a method of training a machine-leaning model using training records augmented with synthetic training records. An exemplary synthetic training records is a synthetic medical record for use in training a model to predict drug overdoses.

18 Claims, 2 Drawing Sheets

(56) References Cited

OTHER PUBLICATIONS

Figure 1:
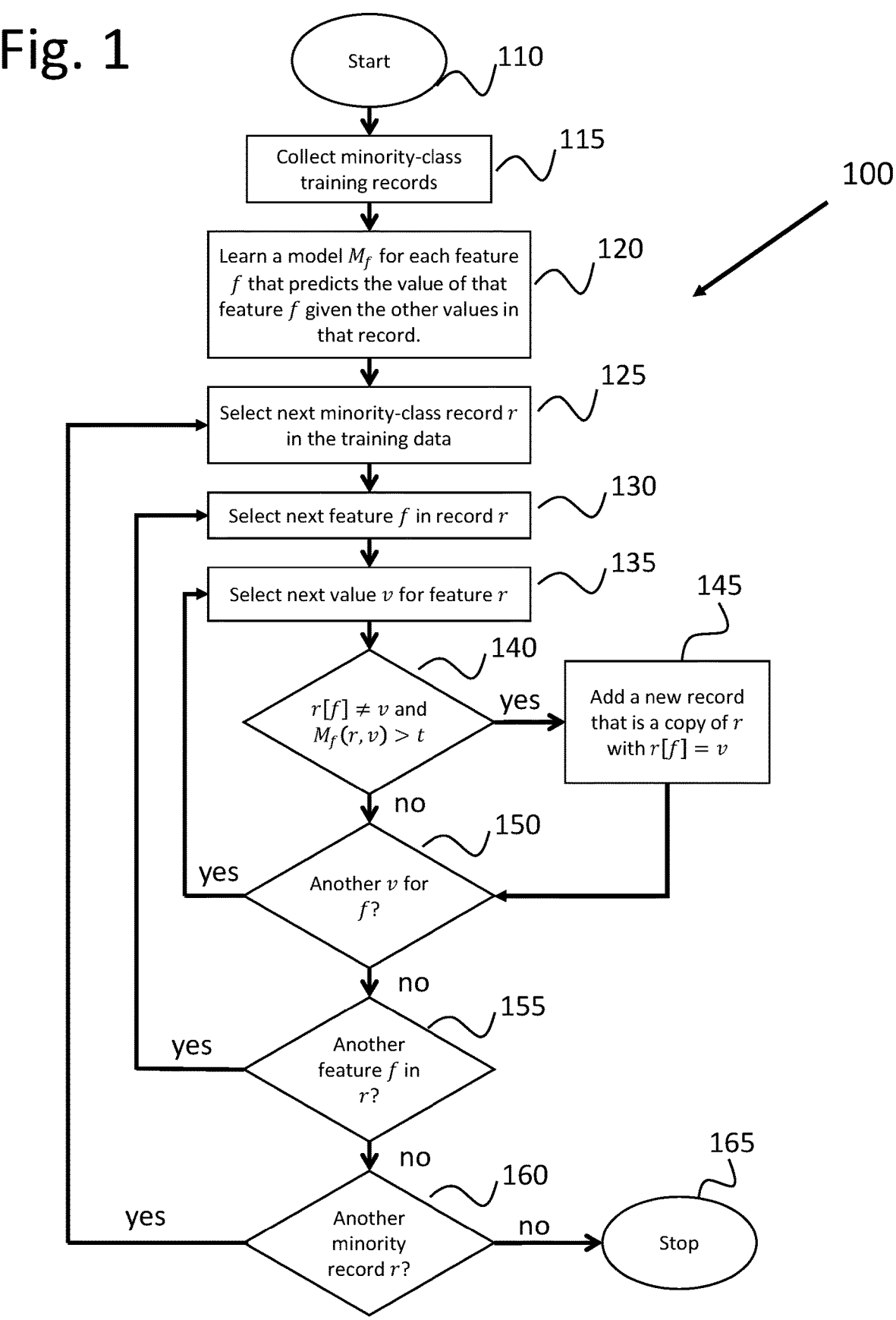

Ribeiro MT et al. "Why Should I Trust You?" Explaining the Predictions of Any Classifier. KDD '16: Proceedings of the 22nd ACM SIGKDD International Conference on Knowledge Discovery and Data Mining. Aug. 2016 pp. 1135-1144 arXiv:1602 04938v3 [cs.LG] Aug. 9, 2016. [retrieved Jan. 21, 2020] Retrieved from the internet: <https://arxiv.org/pdf/1602.04938.pdf>.

sklearn.linear model.LogisticRegression. scikit-learn.org. [Retrieved Jan. 21, 2020] Retrieved from the internet: <https://scikit-learn.org/stable/modules/generated/sklearn.linear_model.LogisticRegression>.

Ribeiro, MT. Tutorial—continuous and categorical features. [Retrieved Jan. 21, 2020] Retrieved from the internet: <https://marcotcr.github.io/lime/tutorials/Tutorial-continuous and categorical features html>.

Ratner AJ et al. Learning to Compose Domain-Specific Transformations for Data Augmentation. arXiv:1709.01643v3 [stat.ML] Sep. 30, 2017. Sep. 30, 2017. [retrieved Jan. 24, 2020] Retrieved from the internet: <https://arxiv.org/pdf/1709.01643.pdf>.

Choi E et al. Generating Multi-Label Discrete Patient Records using Generative Adversarial Networks. arXiv:1703.06490v3 [cs.LG] Jan. 11, 2018. Jan. 11, 2018. [retrieved Jan. 24, 2020] Retrieved from the internet: <https://arxiv.org/pdf/1703.06490.pdf>.

\* cited by examiner

FEATURE PREDICTION

CROSS-REFERENCE TO RELATED APPLICATIONS

This application claims the benefit of U.S. Provisional Application No. 62/680,431, filed on Jun. 4, 2018, which is hereby incorporated by reference in its entirety.

BACKGROUND OF THE INVENTION

The field of the invention is machine learning.

One challenge in machine learning occurs when one wants to predict a class of low-incidence events, events that happen infrequently. For example, one may want to train a model that uses medical records to predict who will overdose on opioids in the coming year. After training such a model, one could reach out to those predicted to be most at risk and intervene, possibly saving lives.

The classic machine learning paradigm is to train a model on examples where one already knows the outcome. In our example, one could look at a previous year and note who overdosed in the next year. Those people that did overdose would get a label of 1, and those that did not would get a label of −1. The standard method is to train the model on these records to maximize its accuracy. Then one can apply this model to a current dataset to predict who will overdose in the next year.

The problem with this approach is that, although far too common, overdoses are low-incidence events. People who overdose in a particular year are rare relative to those who do not. In a sample of medical records corresponding to a general population, the number of records corresponding to patients who overdosed in a particular year may be a very small fraction of the medical records corresponding to the entire population. If randomly-selected records from the general population are used to train a model, the model may learn to simply predict that no one will overdose and still be pretty accurate. This makes it difficult to predict who will overdose.

One approach to this problem of imbalanced classes is oversampling. One can create copies of the minority class and use those multiple copies in the training data so that the classes are more balanced. The problem with this oversampling approach is that the copies do not add any new information, and so the model tends to overfit and learn to identify instances of only those copied records, and it then does poorly on new data.

Another approach is to do undersampling, whereby the algorithm throws out many of the majority class records (the people who did not overdose) to make the classes more balanced. This undersampling approach has the disadvantage of throwing away data, which also hurts the model when it tries to classify unseen data when it is deployed.

One technological approach to get around these difficulties of oversampling or undersampling is to augment the minority class with records that look like minority class records but are not exact copies, which is referred to as data augmentation. An existing method for data augmentation is called Synthetic Minority Oversampling Technique (SMOTE). The way that SMOTE works is for each example in the desired class, it finds the set of nearest neighbors also in that class and adds additional desired-class examples in between those pairs. The problem is that SMOTE does not work well in high-dimensional space because the concept of "nearness" breaks down (this phenomenon is called the "curse of dimensionality"). A high-dimensional space typically refers to a space with at least 10 dimensions, although some search spaces may have hundreds or thousands of dimensions. In a high-dimensional space, the volume of the space increases so quickly, as new records are added, that the data become sparse. This sparsity is problematic for computational predictive models and other computational analytical methods that compare similarity between records because the size of the record space grows exponentially with the dimensionality. Also, organizing and searching data often relies on detecting areas where objects form groups with similar properties. In high dimensional data, however, all objects appear to be sparse and dissimilar in many ways, which prevents common data organization strategies from being efficient. One often wants to identify objects that are near each other, under a well-defined distance metric, but conventional distance metrics and proximity functions are not efficient or reliable. In short, when data are sparse, it is less likely that records will have others nearby, and it becomes harder and more inefficient to computationally identify nearby records. This technological problem presents particular challenges for methods that generate synthetic records because those synthetic records should be similar or near to existing records of the same class.

BRIEF SUMMARY

Disclosed is an embodiment of a computer-implemented method of augmenting a collection of training records for machine learning, comprising storing a plurality of minority-class training records in non-transitory storage media, including a first minority-class training record, wherein each of the plurality of minority-class training records is one of a collection of machine-learning training records comprising training data, said training data comprising a plurality of features, including a first feature, and a classification comprising different first and second classification values, wherein the classification of each of the minority-class training records comprises the first classification value; using a computational process, identifying a different value for the first feature in the first minority-class training record, where the probability of the first feature having the different value exceeds a probability threshold; generating a first synthetic minority-class training record from the first minority-class training record, comprising changing the value of the first feature in the first minority-class training record to the different value; and storing the first synthetic minority-class training record in non-transitory storage media.

Training records in an exemplary embodiment are high-dimensional. In an exemplary embodiment, the training records are medical records, and the classification is drug overdoses.

Also disclosed is a computer-usable non-transitory storage medium comprising a plurality of machine-learning training records, comprising a plurality of minority-class training records and one or more synthetic minority-class training records, wherein each of the one or more synthetic minority-class training records has been generated by the computer-implemented method of augmenting a collection of training records for machine learning.

Also disclosed is a computer-implemented method of training a computer-implemented machine learning model, comprising storing on a computer-usable non-transitory storage media a collection of machine-learning training records comprising training data adapted and configured for the machine learning model, said training data comprising a plurality of features, including a first feature, and a classification, said collection of machine-learning training records comprising a plurality of minority-class training records; creating an augmented collection of machine-learning training records comprising the plurality of minority-class training records and one or more synthetic minority-class training records generated using the computer-implemented method of augmenting a collection of training records for machine learning, and storing said augmented collection of machine-learning training records on the computer-usable non-transitory storage media; and training the computer-implemented machine-learning model with the augmented collection of machine-learning training records.

FIGURES

FIG. 1 describes the steps of an exemplary method of feature prediction for minority class data augmentation.

Figure 2:
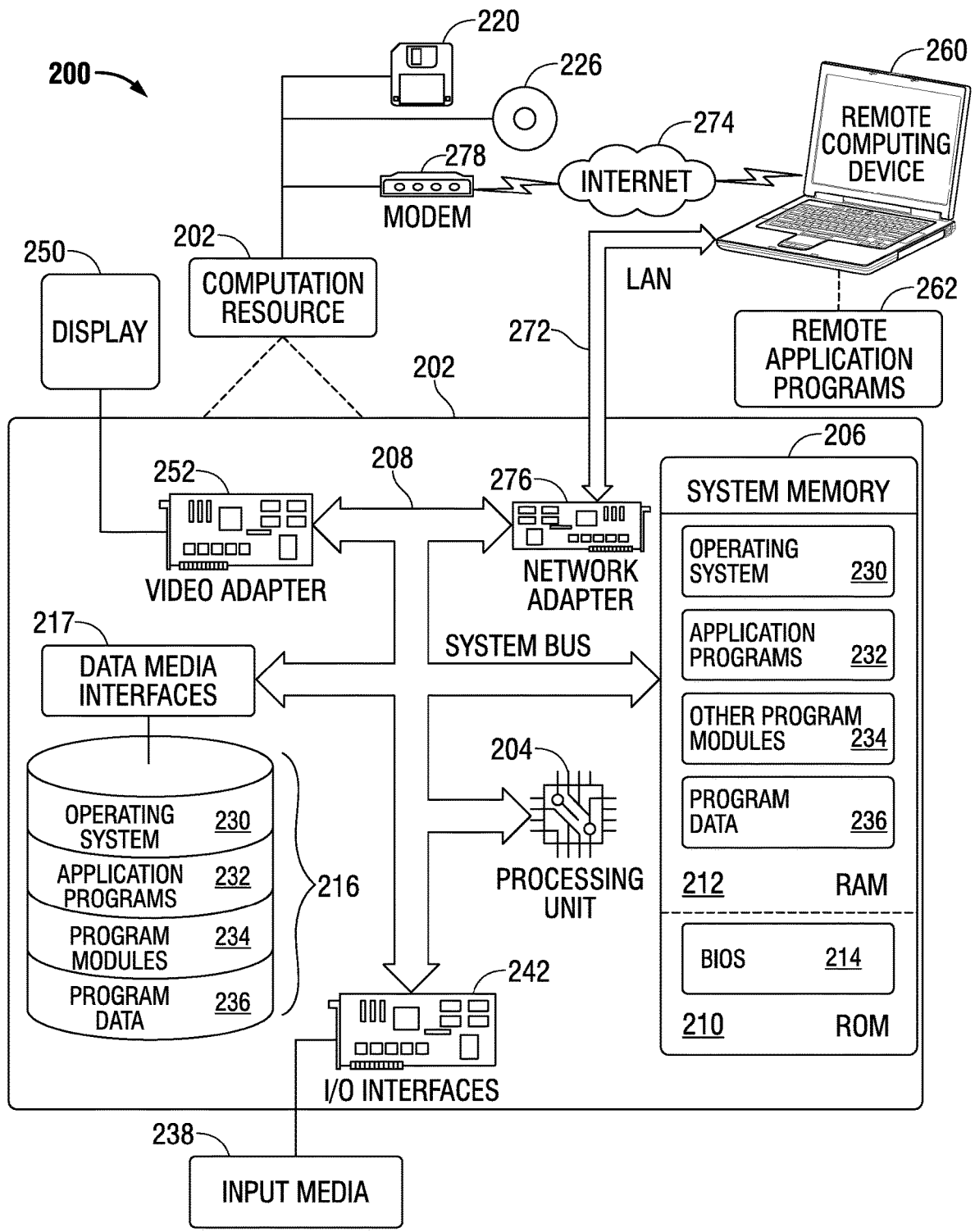

FIG. 2 illustrates an exemplary computer environment for implementing the methods described herein.

DETAILED DESCRIPTION

An exemplary approach is to augment minority class data by learning to generate variations of the minority class records that are still likely to be in that minority class. Data records consist of a set of features, and for each feature, we learn a model that can predict the likely values of that feature given the other features in the record. If the feature model says that the feature could have had a value other than the value it does have, we create a new record that is a copy of the original record but with the feature set to the predicted value. Embodiments applied to high-dimensional spaces surmount or get around the "curse of dimensionality" by not looking for pairs of "nearby" records and instead changing one or more features of a record to ensure that it is nearby or to create another that is "nearby."

As an example, imagine building a model to classify expensive cars from inexpensive ones. The record for each car has a feature "color" that can take the values "red" or "blue", a feature "seat material" that can take the values "leather", "cloth", or "vinyl", and many other features. We want to do classification, but while we have many records of inexpensive cars, we don't have many examples of expensive cars. We want our algorithm to create new instances of expensive cars.

Given a blue expensive car with cloth material, the algorithm could learn that it could copy this car record and add a new record where the material was leather (because presumably there are some expensive blue cars with leather interior). The algorithm could also learn that it could copy the original record and add a new record where the color of the car was red. But since vinyl material is not associated with our set of expensive cars, the model would not be able to copy this record and replace it with one with vinyl material.

A model is a function that maps data records to labels. In an exemplary embodiment, the data records are medical records, and the labels are "overdose" and "no overdose." Data records with labels are used to train the model. After training, this model is used to predict the likely labels of data records without labels. For example, we may have the medical records of a group of people as well as data on whether each had an overdose on opioids. These records can be fed into a model, which then learns to predict whether some new patient (based on her medical records) will overdose. As a further concrete case, one machine may read the medical records of an individual, pass those records to the model, and receive back a prediction. It may then use that prediction to determine whether the person should receive a letter warning them of the dangers of opioids. A model can also be thought of as a function that maps data to a decision or choice. For example, the decision could be whether a person is likely to overdose on opioids.

Medical records (or electronic health records) are high-dimensional because of the number of different features that can determine or be measured with respect to health. Medical records typically include 10 to 1000 dimensions.

In an exemplary embodiment, the model function is a software program, package, or suite of software applications. The software includes computer instructions, and is stored in computer-readable media. The function of the model is performed by one or more computer processors executing the computer instructions. The input medical records preferably are data records stored in computer-readable media.

We now explain the algorithm in detail as shown in FIG. 1.

Step 115 is to collect all of the records in the minority class. Each record consists of a set of features where each feature has a value. Each record in the minority class, in an embodiment, is stored in a computer-readable media.

Step 120 is then to learn a model that predicts the value of each feature given all of the other values of the features for that record. This model is learned over those minority class records collected in step 115. For example, if there are four features in the records from step 115, then step 120 will learn four models, and the model for feature f is represented with the notation $M_f$. The model $M_f(r, v)$ takes a record r and gives the probability of feature f having value (or class or classification) v. These feature models can be learned (or trained) using, for example, logistic regression. In an embodiment in which every feature is a binary classification, a binary logistic regression model can be used. In an embodiment in which a feature may have more than two classifications, a multinomial logistic regression can be used. In an alternative embodiment, a feature with categorical or multiple classes (multi-class) can be represented as binary values using "one-hot" encoding. An exemplary logistic regression model for use with embodiments can be found in the software library scikit-learn at https://scikit-learn.org/stable/modules/generated/skleam.linear_model-.LogisticRegression.html, which is hereby incorporated by reference.

After the feature models are learned, the method loops through the minority class records and makes a copy of each record where a feature model says that its feature is likely to have some other value. Step 125 loops over the minority class records, and considers each record r one at a time. Step 130 loops over the features for record r and considers each feature f one at a time. Step 135 loops over each possible value for feature f and considers each value v one at a time.

Step 140 computes whether the current value for record r for feature f is equal to v, and if it is not, it computes whether the probability of feature f having value v is greater than a threshold t, represented by $M_f(r, v) > t$. If both of these conditions are satisfied, step 145 adds a new record to the set of augmented records. This new record is a copy of record r where feature f is set to have value v. After all of the records have been processed, the algorithm stops in step 165. In an embodiment, the value of t is 0.2. In alternative embodiments, the value may range between any of these ranges: 0.175-0.25, 0.2-0.3, 0.2-0.4, 0.3-0.4, 0.2-0.5, 0.3-0.5, 0.4-0.5, 0.2-0.6, 0.3-0.6, 0.4-0.6, 0.5-0.6, 0.2-0.7, 0.3-0.7, 0.4-0.7, 0.5-0.7, 0.6-0.7, 0.175-0.5, and 0.175-0.7.

The result is a set of augmented records that can be used along with the minority class records during training. These augmented records have the label of the minority class. The augmented records, in an embodiment, are stored in a computer-readable media.

In an embodiment relevant to the study of opioid overdoses, the overdose would be the class or classification, will this person overdose or not? The features are the aspects of the person the model uses to classify whether the person will overdose, such as age and whether that person is currently taking opioids.

We looked at processed binary medical-data records to determine who would overdose in the next year. Each record had 73 binary features. For training, there were 133,728 records, where 744 of those were positive. For testing, there were 2,828 records, where 17 were positive. "Positive" means that an overdose occurred in the following year.

When we used our feature prediction model, it added 7,923 positive training records to the training set, giving 8,667 positive training records. The augmented set of training records (including the synthetic positive records) were fed to the training model. We call this condition "real+pred" and the condition where the prediction algorithm was not used is called "only_real." We also consider two conditions for evaluation:
  a. Balanced means the positive records in the test set were oversampled so there were as many positive as negative. This makes the accuracy meaningful.
  b. Raw means like it was with 17 positive records, where the system can always predict "negative" and have an accuracy of 99%.

The results are shown in table 1 below. F1 is the F1 Score and AUC is area under the curve (receiver operating characteristic).

TABLE 1

|  | Accuracy | Raw F1 | AUC | Accuracy | Balanced F1 | AUC |
| --- | --- | --- | --- | --- | --- | --- |
| only_real | .994 | 0 | .765 | .499 | 0 | .765 |
| real+pred | .985 | .157 | .795 | .612 | .378 | .795 |

We see that the "real+pred" condition does much better on everything other than raw accuracy. Raw accuracy doesn't mean much here because the "only_real" condition classified all records as being negative (not overdose). This is also why F1 is 0 for "only_real."

FIG. 2 illustrates an example of a general computer environment 200 useful in the context of the environments of FIG. 1, in accordance with an implementation of the disclosed subject matter. The general computer environment 200 includes a computation resource 202 capable of implementing the processes described herein. It will be appreciated that other devices can alternatively used that include more components, or fewer components, than those illustrated in FIG. 2.

The illustrated operating environment 200 is only one example of a suitable operating environment, and the example described with reference to FIG. 2 is not intended to suggest any limitation as to the scope of use or functionality of the implementations of this disclosure. Other computing systems, architectures, environments, and/or configurations can be suitable for implementation and/or application of the subject matter disclosed herein.

The computation resource 202 includes one or more processors or processing units 204, a system memory 206, and a bus 208 that couples various system components including the system memory 206 to processor(s) 204 and other elements in the environment 200. The bus 208 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols. Bus 208 may include logical and physical interconnection, including a network or WAN connection, to operationally couple one or more system components located remotely to other system components coupled to Bus 208.

The computation resource 202 may include computers or processors operating in parallel, including architectures in which some of the parallel computers or processors are remote and/or virtual. Computation resource 202 may be implemented on one or more servers that perform the software functions in a hosted Software As A Service (SAAS) environment.

The system memory 206 includes nonvolatile read-only memory (ROM) 210 and random access memory (RAM) 212, which may or may not include volatile memory elements. A basic input/output system (BIOS) 214, containing the elementary routines that help to transfer information between elements within computation resource 202 and with external items, typically invoked into operating memory during start-up, is stored in ROM 210. System memory 206 may contain non-volatile or volatile memory components located remotely and coupled to computation resource 202 by conventional logical and/or physical interconnections, including a network or WAN connection.

The computation resource 202 further can include a non-volatile read/write memory 216, represented in FIG. 2 as a hard disk drive, coupled to bus 208 via a data media interface 217 (e.g., a SCSI, ATA, or other type of interface); a magnetic disk drive (not shown) for reading from, and/or writing to, a removable magnetic disk 220 and an optical disk drive (not shown) for reading from, and/or writing to, a removable optical disk 226 such as a CD, DVD, or other optical media. Non-volatile read/write memory 216 may include one or more non-volatile memory components located remotely and coupled to computation resource 202 by conventional logical and/or physical interconnections, including a network or WAN connection.

The non-volatile read/write memory 216 and associated computer-readable media provide nonvolatile storage of computer-readable instructions, data structures, program modules and other data for the computation resource 202. Although the exemplary environment 200 is described herein as employing a non-volatile read/write memory 216, a removable magnetic disk 220 and a removable optical disk 226, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 216, magnetic disk 220, optical disk 226, ROM 210, or RAM 212, including an operating system 230, one or more application programs 232, other program modules 234 and program data 236. Examples of computer operating systems conventionally employed include LINUX,® Windows® and MacOS® operating systems, and others, for example, providing capability for supporting application programs 232 using, for example, code modules written in the C++® computer programming language or an interpreted language such as Python.

A user can enter commands and information into computation resource 202 through input devices such as input media 238 (e.g., keyboard/keypad, tactile input or pointing device, mouse, foot-operated switching apparatus, joystick, touchscreen or touchpad, microphone, antenna etc.). Such input devices 238 are coupled to the processing unit 204 through a conventional input/output interface 242 that is, in turn, coupled to the system bus. A monitor 250 or other type of display device is also coupled to the system bus 208 via an interface, such as a video adapter 252. One or more remote input devices or display devices may be coupled to computation resource 202 by conventional logical and/or physical interconnections, including a network or WAN connection.

The computation resource 202 can include capability for operating in a networked environment using logical connections to one or more remote computers, such as a remote computer 260. The remote computer 260 can be a personal computer, a server, a router, a network PC, a peer device or other common network node, and typically includes many or all of the elements described above relative to the computation resource 202. In a networked environment, program modules depicted relative to the computation resource 202, or portions thereof, can be stored in a remote memory storage device such as can be associated with the remote computer 260. By way of example, remote application programs 262 reside on a memory device of the remote computer 260. The logical connections represented in FIG. 2 can include interface capabilities, a storage area network (SAN, not illustrated in FIG. 2), local area network (LAN) 272 and/or a wide area network (WAN) 274, but can also include other networks.

Such networking environments are commonplace in modern computer systems, and in association with intranets and the Internet. In certain implementations, the computation resource 202 executes an Internet Web browser program (which can optionally be integrated into the operating system 230), such as the "Internet Explorer®" Web browser manufactured and distributed by the Microsoft Corporation of Redmond, Wash.

When used in a LAN-coupled environment, the computation resource 202 communicates with or through the local area network 272 via a network interface or adapter 276. When used in a WAN-coupled environment, the computation resource 202 typically includes interfaces, such as a modem 278, or other apparatus, for establishing communications with or through the WAN 274, such as the Internet. The modem 278, which can be internal or external, is coupled to the system bus 208 via a serial port interface.

In a networked environment, program modules depicted relative to the computation resource 202, or portions thereof, can be stored in remote memory apparatus. It will be appreciated that the network connections shown are exemplary, and other means of establishing a communications link between various computer systems and elements can be used.

A user of a computer can operate in a networked environment using logical connections to one or more remote computers, such as a remote computer 260, which can be a personal computer, a server, a router, a network PC, a peer device or other common network node, a laptop computer, notebook computer, palm top computer, network computer, smart phone, tablet, or other mobile device, or any processor-controlled device capable of performing the steps, methods, and functions described herein. Typically, a remote computer 260 includes many or all of the elements described above relative to the computer 200 of FIG. 2.

Embodiments described herein can be implemented on an Amazon g2.2×large GPU machine, an Amazon c4.8×large, or a multi-core CPU machine. The computer system may be implemented using other computer architectures (for example, a client/server type architecture, a mainframe system with terminals, an ASP model, a peer to peer model, and the like) and other networks (for example, a local area network, the internet, a telephone network, a wireless network, a mobile phone network, and the like), and those other implementations are within the scope of the invention since the invention is not limited to any particular computer architecture or network.

The computation resource 202 typically includes at least some form of computer-readable media. Computer-readable media can be any available media that can be accessed by the computation resource 202. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 202.

Communication media typically embodies computer-readable instructions, data structures, program modules. By way of example, and not limitation, communication media include wired media, such as wired network or direct-wired connections, and wireless media, such as acoustic, RF, infrared and other wireless media. The scope of the term computer-readable media includes combinations of any of the above.

More specifically, in the computer-readable program implementation, the programs can be structured in an object-orientation using an object-oriented language such as Java, Smalltalk or C++, an interpreted language such as Python, and the programs can be structured in a procedural-orientation using a procedural language such as COBOL or C. The software components communicate in any of a number of means that are well-known to those skilled in the art, such as application program interfaces (API) or interprocess communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in general computer environment 200 in FIG. 2, or on at least as many computers as there are components.

With reference to FIGS. 1 and 2, the steps of algorithm 100 are preferably performed by a Feature Predictor software application program, package, or suite of software applications that realize the model $M_f$ and/or, in an embodiment, generative model 320. The Feature Predictor software preferably is stored with other Application Programs 232 in non-volatile read/write memory 216 and includes instructions that, when executed by the one or more processing units 204, cause the computation resource 202 to perform the steps of algorithm 100 and generate one or more augmented records having the label of the training class and store the one or more augmented records in data files with other program data 236 in non-volatile read/write memory 216. Algorithm 100 operates on minority class records that have been stored in date files with other program data 236 in non-volatile read/write memory 216. In an embodiment, the one or more augmented records having the label of the training class combined with the minority class records in a training data file that is stored with other program data 236 in non-volatile read/write memory 216. Predictive model 370, explanatory model 370, and certainty model 350 are similarly realized in a software application program, package, or suite of software applications.

The terms and descriptions used herein are set forth by way of illustration only and are not meant as limitations. Those skilled in the art will recognize that many variations are possible with the spirit and scope of the invention, including as defined in the claim and their equivalents. The described embodiments illustrate the scope of the claim but do not restrict the scope of the claims.

What is claimed is:

1. A computer-implemented method of augmenting a collection of training records for machine learning, the method performed by a computer system, said computer system comprising one or more processors and computer-usable non-transitory storage media operationally coupled to the one or more processors, comprising:

Storing a plurality of minority-class training records in non-transitory storage media, including a first minority-class training record, wherein each of the plurality of minority-class training records is one of a collection of machine-learning training records comprising training data, said training data comprising a plurality of features, including a first feature, and a classification comprising a first classification value and a second classification value, wherein the classification of each of the minority-class training records comprises the first classification value, wherein the training records comprise medical data, the classification comprises a drug overdose, and the first feature can be used to train a computer-implemented machine-learning model to make a drug overdose prediction, using a computational process performed by the one or more processors executing software instructions stored in the computer-usable non-transitory storage media, identifying a different value for the first feature in the first minority-class training record, where the probability of the first feature having the different value in the first minority-class training record exceeds a probability threshold;

generating a first synthetic minority-class training record from the first minority-class training record, comprising changing the value of the first feature in the first minority-class training record to the different value; and adding the first synthetic minority-class training record to the plurality of minority-class training records comprising storing the first synthetic minority-class training record in the non-transitory storage media whereby the plurality of minority-class training records comprises the first minority-class training record comprising the first feature and the first synthetic minority-class training record comprising a different value for the first feature.

2. The computer-implemented method of augmenting a collection of training data records for machine learning of claim 1, wherein each of the machine-learning training records is high-dimensional.

3. The computer-implemented method of augmenting a collection of training data records for machine learning of claim 1, wherein the classification comprises a low-incidence event.

4. The computer-implemented method of augmenting a collection of training data records for machine learning of claim 1, wherein the computational process comprises logistic regression.

5. The computer-implemented method of augmenting a collection of training data records for machine learning of claim 1, wherein the probability threshold is within the range 0.175 to 0.7.

6. The computer-implemented method of augmenting a collection of training data records for machine learning of claim 1, wherein the probability threshold is 0.2.

7. The computer-implemented method of augmenting a collection of training data records for machine learning of claim 1, wherein the first feature is binary.

8. The computer-implemented method of augmenting a collection of training data records for machine learning of claim 1, wherein the first feature is categorical.

9. The computer-implemented method of augmenting a collection of training data records for machine learning of claim 1, wherein the first feature comprises two or more class values.

10. The computer-implemented method of augmenting a collection of training data records for machine learning of claim 1, wherein the first feature can be used by a computer-implemented machine-learning model trained to predict the occurrence of a drug overdose.

11. The computer-implemented method of augmenting a collection of training data records for machine learning of claim 1, wherein the first feature can be used by a computer-implemented machine-learning model to predict the occurrence of a drug overdose.

12. The computer-implemented method of augmenting a collection of training data records for machine learning of claim 1, wherein the first feature can be used by a computer-implemented machine-learning model trained to make a drug overdose prediction.

13. The computer-implemented method of augmenting a collection of training data records for machine learning of claim 1, wherein the first feature can be used to train a computer-implemented machine-learning model to predict the occurrence of a drug overdose.

14. The computer-implemented method of augmenting a collection of training data records for machine learning of claim 1, wherein the classification of the first synthetic minority-class training record comprises the first classification value.

15. A computer-usable non-transitory storage medium comprising a plurality of machine-learning training records, comprising:

a plurality of minority-class training records comprising medical records; and one or more synthetic minority-class training records, wherein each of the one or more synthetic minority-class training records has been generated by the computer-implemented method of augmenting a collection of training records for machine learning of claim 1, and wherein the one or more synthetic minority-class records comprise synthetic medical records adapted for use with a model for predicting drug overdoses.

16. The computer-usable non-transitory storage medium of claim 15 wherein each of the one or more synthetic minority-class records is different from each of the plurality of minority-class training records.

17. A computer-implemented method of training a computer-implemented machine learning model, said computer-implemented machine learning model being implemented on a computer system, said computer system comprising one or more processors and computer-usable non-transitory storage media operationally coupled to the one or more processors, and the non-transitory storage media comprising computer instructions which when executed by the one or more processors perform the functions of the machine learning model, comprising:

Storing on the computer-usable non-transitory storage media a collection of machine-learning training records comprising medical records and further comprising training data adapted and configured for the machine learning model, said training data comprising a plurality of features, including a first feature, and a classification comprising opioid overdose information, said collection of machine-learning training records comprising a plurality of minority-class training records;

Creating an augmented collection of machine-learning training records comprising the plurality of minority-class training records and one or more synthetic minority-class training records generated using the computer-implemented method of augmenting a collection of training records for machine learning of claim 1, and storing said augmented collection of machine-learning training records on the computer-usable non-transitory storage media, and Training the computer-implemented machine-learning model with the augmented collection of machine-learning training records, where training comprises execution by the one or more processors of computer instructions stored in the computer-usable non-transitory storage media.

18. The computer-implemented method of training a computer-implemented machine learning model of claim 17, wherein each of the plurality of minority class training records is high-dimensional.

* * * * *